(12) United States Patent
McGann et al.

(10) Patent No.: US 7,141,786 B2
(45) Date of Patent: Nov. 28, 2006

(54) PARTICLE SAMPLING PRECONCENTRATOR

(75) Inventors: William J. McGann, Raynham, MA (US); Kenneth Ribeiro, North Reading, MA (US)

(73) Assignee: General Electric Company, Schenectady, NY (US)

( * ) Notice: Subject to any disclaimer, the term of this patent is extended or adjusted under 35 U.S.C. 154(b) by 9 days.

(21) Appl. No.: 10/936,112

(22) Filed: Sep. 8, 2004

(65) Prior Publication Data

US 2006/0049346 A1 Mar. 9, 2006

(51) Int. Cl.
*G01N 1/00* (2006.01)

(52) U.S. Cl. ............... 250/287; 250/288; 73/863.12; 73/31.07; 73/864.11; 422/88; 422/99

(58) Field of Classification Search ............... None
See application file for complete search history.

(56) References Cited

U.S. PATENT DOCUMENTS

| | | |
|---|---|---|
| 4,045,997 A | 9/1977 | Showalter et al. |
| 4,202,200 A | 5/1980 | Ellson |
| 4,772,794 A | 9/1988 | Jenkins |
| 4,781,972 A | 11/1988 | Sakane et al. |
| 4,896,547 A | 1/1990 | Arney et al. |
| 4,964,309 A | 10/1990 | Jenkins |
| 4,987,767 A | 1/1991 | Corrigan et al. |
| 5,027,643 A | 7/1991 | Jenkins |
| 5,109,691 A | 5/1992 | Corrigan et al. |
| 5,200,614 A | 4/1993 | Jenkins |
| 5,405,781 A | 4/1995 | Davies et al. |
| 5,491,337 A | 2/1996 | Jenkins et al. |
| 5,585,575 A | 12/1996 | Corrigan et al. |
| 5,741,984 A | 4/1998 | Danylewych-May et al. |
| 5,753,832 A | 5/1998 | Bromberg et al. |
| 5,760,314 A | 6/1998 | Bromberg et al. |
| 5,859,362 A | 1/1999 | Neudorfl et al. |
| 5,859,375 A | 1/1999 | Danylewych-May et al. |
| 5,915,268 A | 6/1999 | Linker et al. |
| 6,073,499 A | 6/2000 | Settles |
| 6,334,365 B1 | 1/2002 | Linker et al. |
| 6,375,697 B1 * | 4/2002 | Davies ........................ 55/340 |
| 6,407,382 B1 | 6/2002 | Spangler |
| 6,435,043 B1 | 8/2002 | Ferguson et al. |
| 6,642,513 B1 | 11/2003 | Jenkins et al. |
| 6,690,005 B1 | 2/2004 | Jenkins et al. |
| 6,732,569 B1 | 5/2004 | Ondov et al. |
| RE38,797 E * | 9/2005 | Linker et al. ............ 73/863.12 |
| 2004/0131503 A1* | 7/2004 | McGann et al. ............ 422/99 |

FOREIGN PATENT DOCUMENTS

EP   0 247 243   12/1987

\* cited by examiner

*Primary Examiner*—Jack Berman
*Assistant Examiner*—Zia R. Hashmi
(74) *Attorney, Agent, or Firm*—Gerald E. Hespos; Anthony J. Casella

(57) ABSTRACT

An apparatus is provided for identifying trace amounts of substances of interest in an air flow. The apparatus includes an inlet for receiving the air flow and an outlet for exhausting major portions of the air flow. The outlet is offset from the inlet. A porous impactor is disposed in alignment with the inlet and is impacted by particles entrained in the air flow. The porous impactor is heated sufficiently to vaporize particles impinging thereon. A detector communicates with the porous impactor and is operative for identifying substances of interest in the vaporized particles.

20 Claims, 4 Drawing Sheets

PARTICLE SAMPLING PRECONCENTRATOR

BACKGROUND OF THE INVENTION

1. Field of the Invention

The invention relates to detectors for detecting trace amounts of particles of interest.

2. Description of the Related Art

Terrorism risks continue to exist at transportation facilities, government buildings and other high profile locations where there is a significant flow of pedestrian or vehicular traffic. As a result, most airports and many government buildings now include apparatus for detecting trace amounts of explosives. These devices typically operate on the principle that small amounts of the explosive materials will be transferred to the body, clothing and luggage of people who had handled the explosive.

Some detectors employ small flexible fabric-like traps that can be wiped across a package or piece of luggage. The trap removes residue from the surface of the package or luggage. The trap then is placed in an apparatus, such as an ion trap mobility spectrometer, that tests the residue on the trap for trace amounts of explosive materials. A device of this type is disclosed in U.S. Pat. No. 5,491,337 and is marketed by the GE Ion Track. These devices typically are employed in proximity to metal detectors at airports, and security personnel will perform screening on some of the passengers based on a random sampling or based on a determination that the passenger has met certain criteria for enhanced screening.

The ion trap mobility spectrometer disclosed in U.S. Pat. No. 5,491,337 also can operate in a mode for detecting trace amounts of narcotics. Narcotics are illegal and insidious. Furthermore, it is known that many terrorists organizations fund their terrorism through the lucrative sale of narcotics.

Only a fraction of airline passengers have their carry-on baggage checked for trace amounts of explosives or narcotics using fabric-like traps and the available ion trap mobility spectrometers or similar devices. Efforts to use such devices to check all carry-on bags for trace amounts of explosives or narcotics would impose greater time and cost penalties on the airline industry. Additionally, the above-described explosive detectors typically are used only on luggage and other parcels. An apparatus of this type would not identify plastic explosives worn by a passenger who had no carry-on luggage.

U.S. Pat. No. 6,073,499 discloses a walk-through detector. The detector shown in U.S. Pat. No. 6,073,499 operates under the principle that a boundary layer of air adjacent to a person is heated by the person. This heated air adjacent a person is less dense than air farther from the person. Less dense air rises. Accordingly, a thermal plume of air referred to as a human convection plume flows up adjacent to the person at a rate of about 50 liters per second. Minute particles, including particles of explosives or narcotics that may have been handled by the person, will be entrained in this human convection plume of air and will flow up from the person. U.S. Pat. No. 6,708,572 shows a walk-through detector with a plurality of high-pressure air jets that direct small puffs of air towards the torso of the person in the portal. These jets of air help to stimulate a release of particles from the clothing and hands of the person so that a greater concentration of particles can become entrained in the human convection plume.

The above-described walk-through detector has a metallic screen incorporated into the ceiling of the portal. A vacuum pump or fan above the screen generates an airflow that is intended to match the volumetric flow of air generated by the human convection plume (e.g., about 50 liters/second). An airflow generated by the vacuum pump or fan that is too low will permit particles entrained in the human convection plume to dissipate into the ambient air on currents of ambient air near the detector. A flow rate generated by the vacuum pump or fan that is too high will draw additional air through the screen and hence will dilute the concentration of particles of interest. Some of the particles entrained in the thermal plume will attach to the screen. The screen in the ceiling of the portal is moved into a desorber after a sufficient sampling time (e.g., 5 seconds) and is heated to temperatures in the range of 220° C.–250° C. so that particles thereon are vaporized. The vaporized particles then are drawn into the inlet of the ion mobility spectrometer, the ion trap mobility spectrometer or other such detecting device to determine whether any particles of interest were entrained in the human convection plume. An alarm or other signal will be triggered if a particle of interest is detected. The above-described walk-through detector typically operates at an overall average sampling efficiency of about 1% at mid-torso level. This level of efficiency typically meets government standards for detection and offers low false alarm rates. Thus, the walk-through detector disclosed in U.S. Pat. No. 6,073,499 and in U.S. Pat. No. 6,708,572 is very effective for detecting whether a person is carrying explosives or narcotics and whether the person has recently handled explosives or narcotics. However, improved efficiencies would be received well and could be even more effective for detecting even smaller amounts of particles of interest without increasing the false alarm rate.

The walk-through detector disclosed in U.S. Pat. No. 6,073,499 and U.S. Pat. No. 6,708,572 is marketed by GE Ion Track as the EntryScan3® and currently operates at about a fifteen second cycle to sample, desorb and analyze a passenger. The person being screened must pause in the portal of the walk-through detector for at least the sampling phase of that cycle, and typically at least about 5 seconds. A system that achieves a shorter cycle time would be well received in the industry.

Inertial impactors use principles enunciated in Stokes Law and function to collect particles entrained in a gas. Such impactors have been used, for example, in the analysis of air quality and are shown, for example, in U.S. Pat. No. 6,435,043 and U.S. Pat. No. 6,732,569. Inertial impactors have not been used to identify extremely small particles (e.g., 1 micron) of explosives or narcotics that may exist at low concentration in an air stream of 50–100 liters per second.

In view of the above, it is an object of the subject invention to provide a detector with improved sample collection efficiency.

Another object of the invention is to provide a detector with a shorter cycle time from sample collection to analysis, and hence a detector with a higher passenger throughput.

A further object of the invention is to provide a detector with fewer or no moving parts.

SUMMARY OF THE INVENTION

The subject invention relates to a preconcentrator for use with a detecting apparatus that analyzes samples of air to determine whether any particles of interest exist in the sample of air. The preconcentrator improves collection efficiency at any selected flow rate. The invention also relates to a detecting apparatus that incorporates such a preconcentrator.

The preconcentrator of the subject invention preferably comprises a flow impactor in the path of the air that is flowing from the person or object being sampled. The impactor is configured to alter the flow path of at least part of the gas in which the particles of interest are entrained. However, particles, including particles of interest, that are entrained in the air stream have greater mass and hence greater inertia than the gas molecules. Thus, the particles, especially those of 1 μm or larger, are less likely to be diverted by the impactor, and accordingly will continue along a more linear path towards the impactor. As a result, the concentration of particles approaching the impactor can be increased significantly. An impactor differs significantly from a screen or filter in that a screen or filter permits the air to pass therethough. The impactor, however, does not pass most of the air, but rather diverts most of the air. The geometry of the impactor can be selected in view of the flow rates and known characteristics of the substances of interest. The impactor may be in the form of a substantially honeycomb with substantially hexagonal spaces.

The detector of the subject invention preferably is configured to sample and analyze continuously rather than employing the sample/desorb/analyze cycle of known devices. The continuous operation can be achieved by providing an impactor that can be heated sufficiently to desorb the particles of interest or an impactor that can be used in combination with such a continuous heater. In this regard, the impactor may be formed from a metallic sintered material that can be heated to sufficiently high temperatures to vaporize or desorb particles impinging thereon. Alternatively, the impactor can be formed from a non-metallic or ceramic sintered material that is plated with metal. The metal material of the impactor can have an electric current applied thereto. The current is controlled to heat the impactor sufficiently to vaporize particles impinging thereon. Air flowing through the impactor will transport the vaporized particles of interest to the inlet to the detector. Thus, the detector has the potential of operating substantially continuously at a passenger throughput rate of 5 seconds or less.

DETAILED DESCRIPTION OF THE PREFERRED EMBODIMENTS

Figure 1:
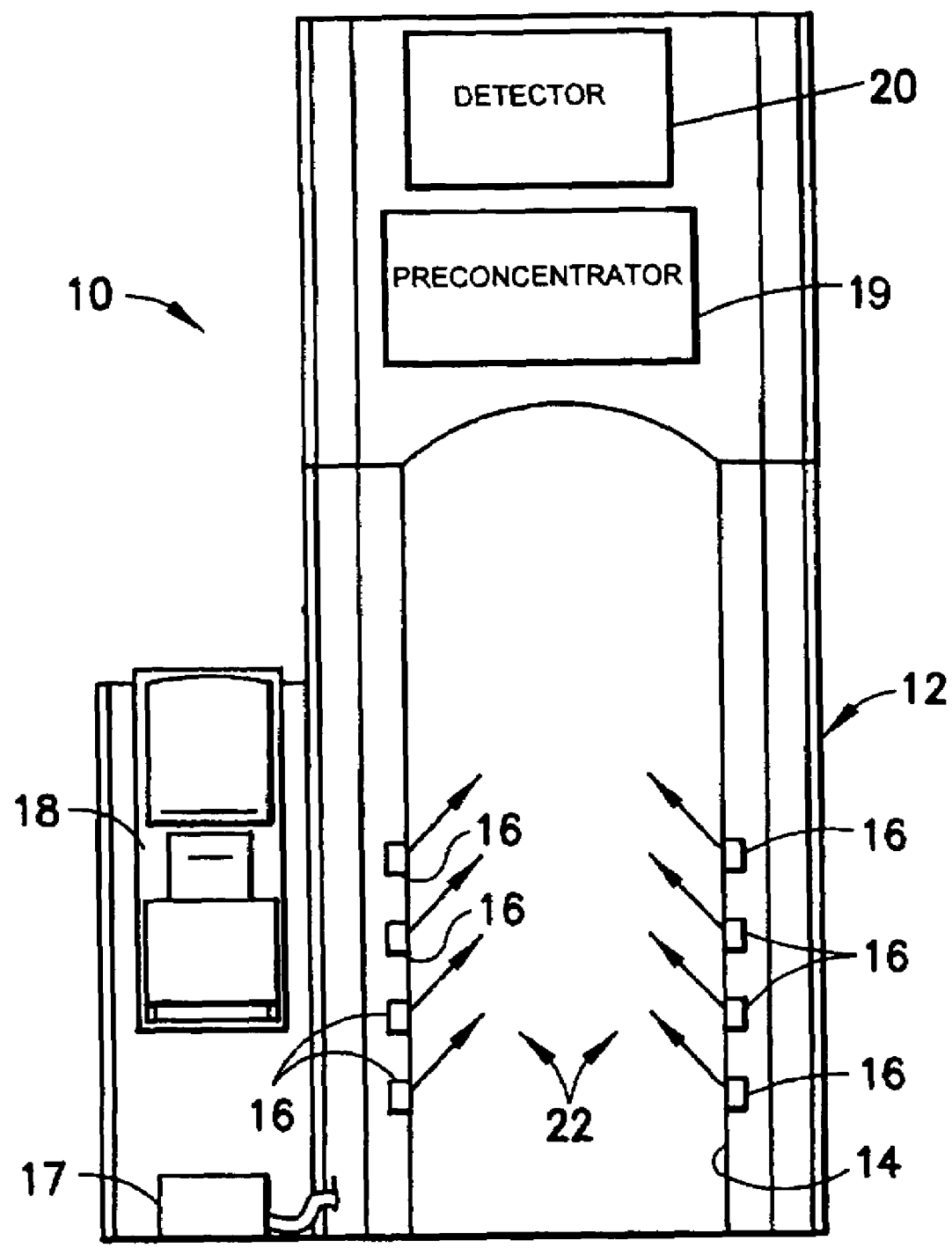
FIG. 1 is a schematic view of a walk-through portal that incorporates the preconcentrator and detector of the subject invention.

A portal detection system that incorporates the preconcentrator and detector of the subject invention is identified generally by the numeral 10 in FIG. 1. The portal detection system 10 includes a portal 12 that is similar to the portal disclosed in U.S. Pat. No. 6,073,499 and U.S. Pat. No. 6,708,572. More particularly, the portal 12 has a passage 14 extending therethrough. The portal 12 typically will be installed at a security checkpoint and the passage 14 thereof will be dimensioned to conveniently accommodate a human pedestrian who desires clearance at the security checkpoint.

The portal detection system 10 operates partly upon the theories described in U.S. Pat. No. 6,073,499. In particular, a boundary layer of air adjacent to a person is heated by the person and generally is hotter than ambient air at farther distances from the person. Hot air is less dense than cooler air and rises relative to the more dense cooler air. As a result, a significant human convection plume of hot air rises in the boundary area adjacent to the person. The human convection plume generally achieves flow rates of 50–100 liters/second. This significant flow of warm air tends to entrain particles that had been on the skin or clothing of the person passing through the portal 10. Thus, these microscopic particles travel upwardly with the plume of heated air.

The portal 10 includes air jets 16 that direct short puffs of air towards the person in the passage 14. The jets 16 are directed at an area of the person extending roughly from the knees to the mid torso and help to dislodge particles from the skin and clothing to stimulate particle separation and hence to increase the concentration of particles entrained in the human convection plume. The portal detector apparatus 10 further includes a compressed air supply 17 that is controlled to fire the jets sequentially from bottom to top as explained in U.S. Pat. No. 6,708,572. However, other jet firing patterns can be used.

Figure 2:
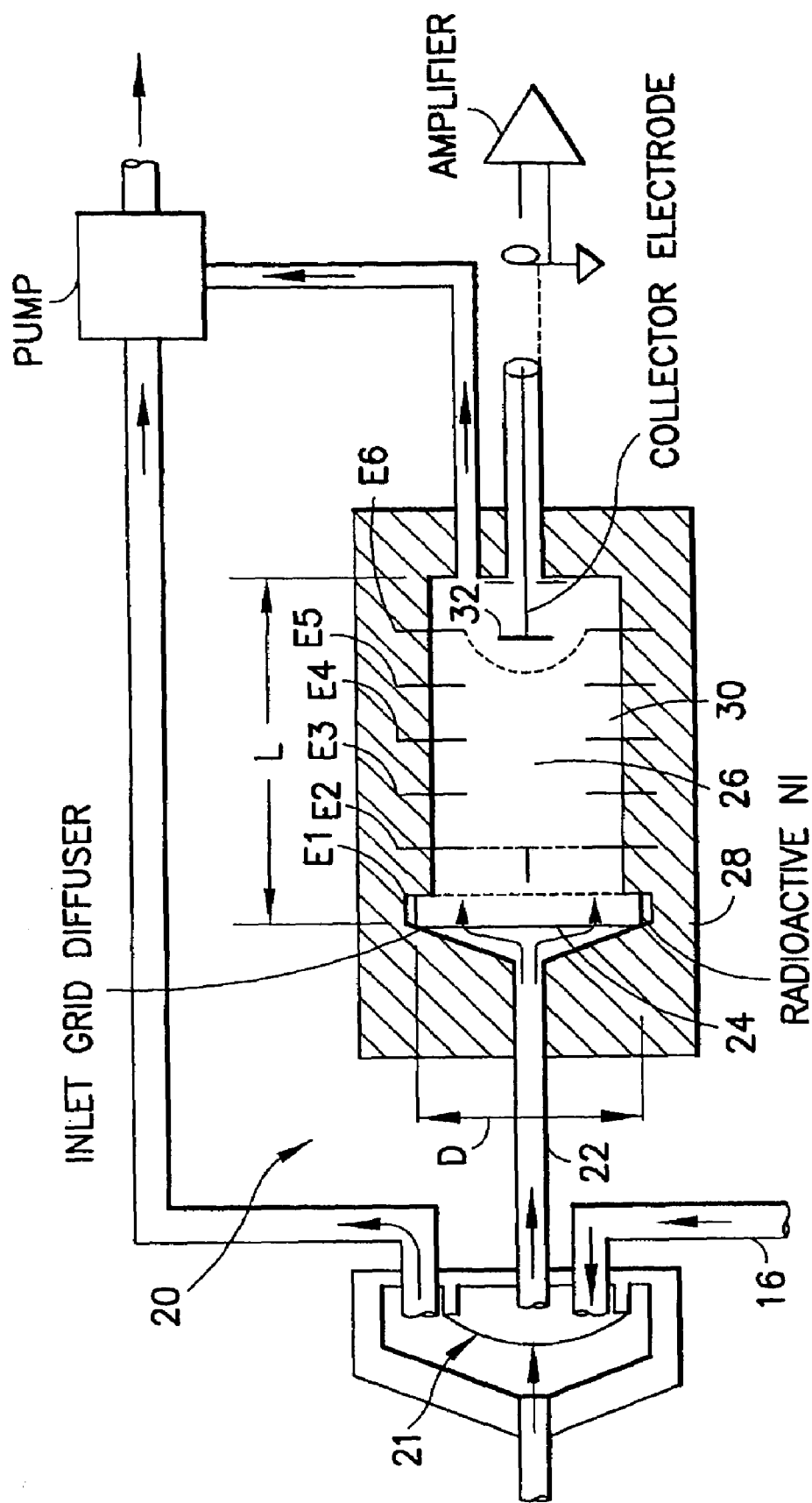
FIG. 2 is a schematic diagram of a known ion trap mobility spectrometer that can be used with the preconcentrator of the subject invention.

The portal detection apparatus 10 further includes a controller 18, a preconcentrator 19 and a detector 20. The detector 20 preferably is an ion trap mobility spectrometer as disclosed in U.S. Pat. No. 5,491,337 and as illustrated schematically in FIG. 2. More particularly, the detector 20 includes a heated membrane 21 formed from a microporous refractory material or from dimethyl silicone and disposed to communicate with a portion of the airflow generated by the thermal plume in the passage 14 of the portal detector apparatus 10. The heated membrane 21 blocks passage of at least selected constituents of the air but enables passage of other constituents of the air, including the constituents of interest.

The sample air, carrier gas, and dopant molecules pass through the inlet 22 and are spread by a diffuser 24 into an ionization chamber 26. The ionization chamber 26 is in the form of a shallow cylinder with a diameter D, length L, and cylindrical wall 28 of a radioactive material, e.g., nickel$^{63}$ or tritium, which emits beta particles. Inlet 22 communicates with one end of the ionization chamber 26. A grid electrode $E_1$ is provided at the end opposite the inlet 22, and is normally maintained at the same potential as the inlet end and the walls of the ionization chamber 26. Thus a largely field-free space is provided in which electrons and ion charges build up and interact with the sample molecules under bombardment by the beta-particles from the radioactive walls. Beyond the ionization chamber 26, the ionized sample gases pass through open electrode $E_1$ and into an ion drift region 30 having several field-defining electrodes $E_2$–$E_n$. A collector electrode or plate 32 is disposed at the end of the drift region 30 for receiving the ion samples reaching that end. Periodically a field is established across the ionization region 26, by creating a potential difference between the grid electrode $E_1$ and the inlet diffuser 24 and radioactive source 28, for about 0.1–0.2 mS, to sweep the ions through the open grid $E_1$ into the drift region 30 with the assistance of the switching of the field between electrodes $E_1$ and $E_2$. The ions in the drift region 30 experience a constant electric field, maintained by the annular electrodes $E_2$–$E_n$, impelling them along the region and down toward the collector electrode 32. The electrode 32 detects the arriving charge, and produces signals that are amplified and analyzed through their spectra in the spectrometer. The gases exit through an outlet in the wall next to the electrode 32. After about 0.2 mS the field across the ionization region 26 is again reduced to zero and the ion population is again allowed to build up in the chamber 26 preparatory to the imposition of the next field. The polarity of the fields is chosen on the basis of whether the detector is operated in a negative or positive ion mode. When detecting explosives, a negative ion mode is usually appropriate, but when detecting narcotic samples positive ion mode is preferred.

Figure 3:
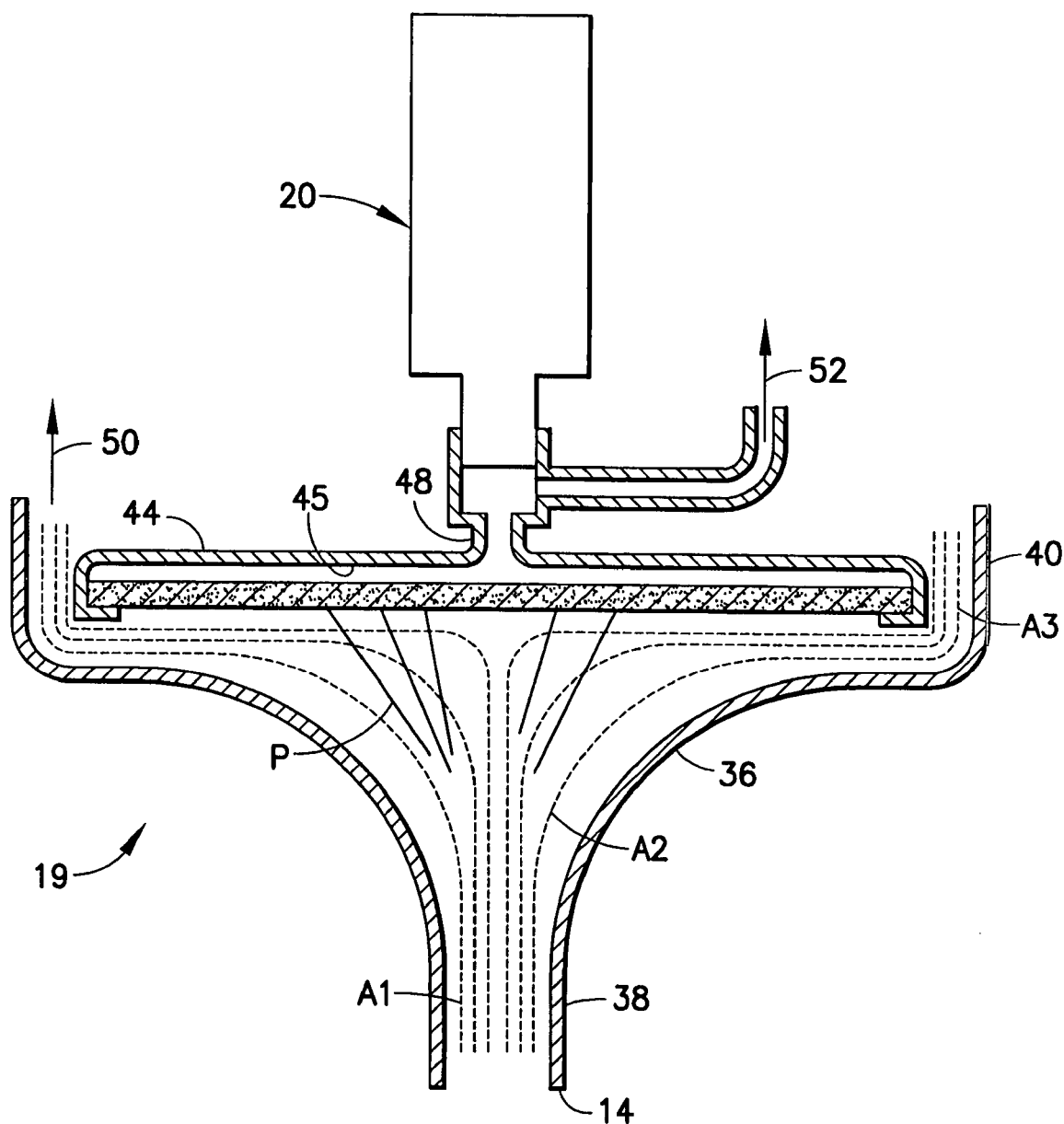
FIG. 3 is a cross-sectional view taken along a vertical line and illustrating a first embodiment of a preconcentrator according to the subject invention.
Figure 4:
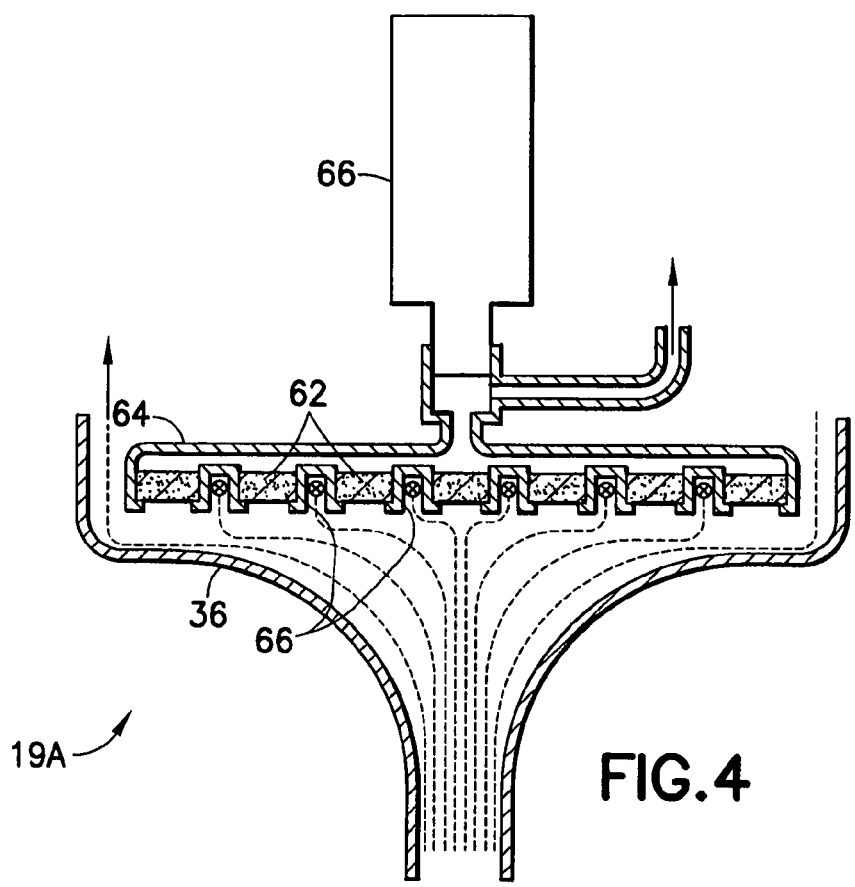
FIG. 4 is a cross-sectional view similar to FIG. 3, but showing a preconcentrator in accordance with a second embodiment of the invention.
Figure 5:
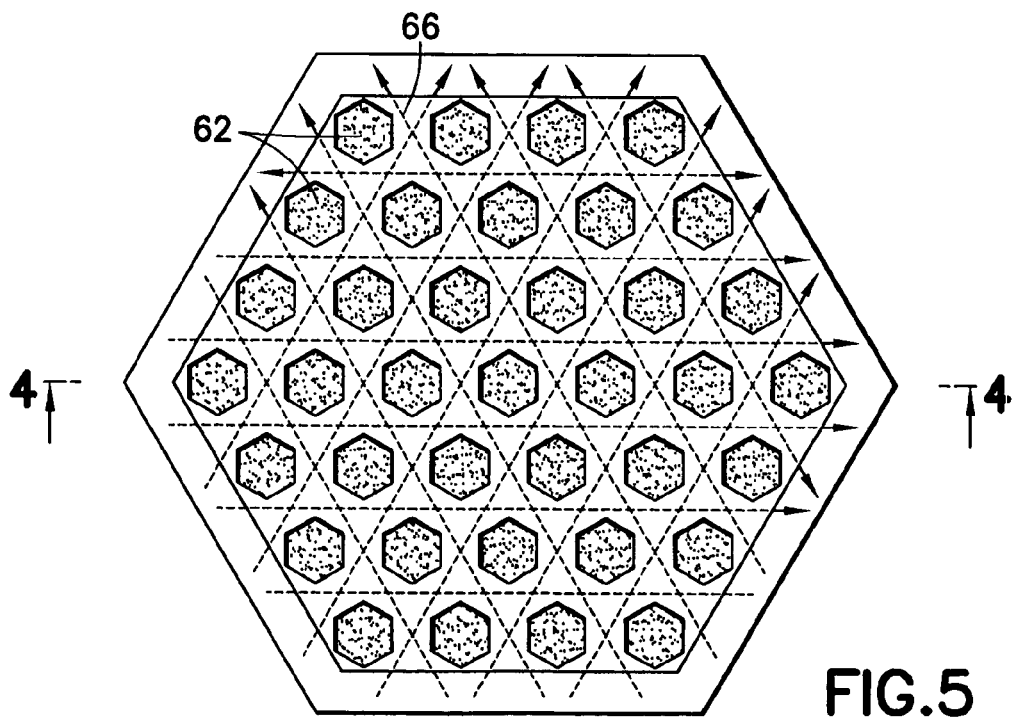
FIG. 5 is a plan view of the impactor incorporated into the preconcentrator of FIG. 4.

The preconcentrator 19 of the subject invention is disposed between the passage 14 and the detector 20 as shown in FIG. 3. The preconcentrator 19 includes a channel 36 with an inlet 38 and an outlet 40. A porous impactor 42 is mounted in proximity to the outlet 40 and is sufficiently small to permit a main sample exhaust flow between the periphery of the porous impactor 42 and the outlet 40 of the channel 36. A chamber 44 is mounted to the porous impactor 42 and defines a plenum 45 that surrounds a side of the porous impactor 42 opposite the inlet 38 to the channel 36. The plenum 45 includes an outlet 46 that communicates with the inlet 22 of the detector 20. A main sample air pump 50 communicates with the outlet 40 of the channel 36 and generates an air flow rate that approximately matches the flow rate of the human convection plume (e.g. 50–100 liters/second). A detector sample air pump 52 communicates with the outlet 46 from the plenum 45 and with the detector 20 and produces a much lower flow rate that matches the flow rate preferred for the detector (e.g. 300 cc/mim).

The porous impactor 42 creates an impediment to the substantially linear flow of air A1 in the inlet 38 to the channel 36. Gaseous molecules in the flow of air A1 in the inlet 38 have very low inertia due to their low mass and density. Hence, a significant portion of the gaseous molecules in the flow A1 will be diverted through curved paths indicated generally by A2 in FIG. 3 to bypass the porous impactor 42 and to follow a path A3 between the outer periphery of chamber 44 and the outlet 40 of the channel 36. The flows A1 and A3 are offset and do not align. Particles P entrained in the inlet airflow A1 have more mass and higher density than the gaseous molecules and hence have more inertia. Accordingly, particles P entrained in the inlet air flow A1 will follow more linear paths towards the porous impactor 42. As a result, the concentration of particles P impinging on the porous impactor 42 will exceed the concentration of particles in the inlet 38.

The main sample air pump 50 is operative to generate airflow rates approximately equal to the airflow rates in the human convection plume. As noted above, airflow rates in the human convection plume surrounding the person in the portal 10 typically are in the range of 50–100 liters/second. The size and shape of the channel 36 and the size, composition and porosity of the impactor 42 are selected to optimize the concentration of particles P impinging upon and/or passing through the porous impactor 42 and to minimize the concentration of particles by-passing the chamber 44 and exiting the outlet 40. These flow characteristics of the particles P are dependent upon a Stokes number analysis. In this regard, Stokes law relates to the velocity characteristics of an object settling in a fluid, wherein:

$$V_{term} := \left(\frac{1}{18}\right) \cdot \rho \cdot Size_{particle}^2 \cdot \frac{g}{\mu}$$

In this equation, $\rho$ relates to, density between the particle and the fluid, $\mu$ is the viscosity of the fluid and g is the acceleration of gravity. The Stokes number is an index of particle impactability. Molecules with a Stokes number near zero have little inertia and are not impactible. Particles with high Stokes numbers (e.g., approaching 1) are impactible. The Stokes number is determined by the equation $$St := \frac{\rho_{particle} \cdot Size_{particle}^2}{18 \cdot \mu \cdot \tau}$$

In this equation, $\tau$ equals characteristic time which is calculated as Lchr/Vchr, where Lchr is the dimension of the body upon which particle impaction takes place, and Vchr is the relative velocity between the air stream and the body. As noted above, the flow rate of air A1 is about 50 liters per second, and the flow velocity is about 5 meters per second. The porous impactor has an area of about 16 in$^2$.

The angular acceleration produced by the change in directional flow in the preconcentrator 19 is calculated as Acceln=(Velocity Airflow)$^2$/radius This result can be used in a Stokes law equation for calculating particle lag due to inertia by replacing the above-calculated acceleration for the acceleration of gravity considered in the original Stokes law. Thus, Stokes law as applied to particle lag due to inertia is $$V_{particle} := \left(\frac{1}{18}\right) \cdot \rho \cdot Size_{particle}^2 \cdot \frac{acceln}{\mu}$$

The Stokes law relationship can be utilized with changes in geometry and air velocity to maximize impaction of particles on the porous impactor 42. As a result, greater concentrations of particles can be placed in communication with the detector 20, thereby enhancing reliability. The porous impactor 42 is designed using these relationships to collect particles with sizes of 1 micron and larger.

As noted above, existing portal detector devices have a cycle that includes sampling, desorbing and analyzing. Additionally, the known devices typically require a mechanical translation of a sampling screen from a sampling location to the desorber. The cycle time can be reduced significantly in the apparatus 10 by substantially continuously heating the porous impactor 42 in situ sufficiently to desorb particles impinging thereon. The vaporized particles then are transported substantially continuously to the inlet 22 of the detector 20, thereby automatically cleaning the impactor 42. Heating can be achieved by forming the porous impactor from a sintered metal and then passing an electric current through the porous impactor 42 for heating the porous impactor 42 sufficiently to vaporize particles impinging thereon. The chamber 44 also can be heated for maintaining desired temperature of the particles for transfer to the detector 20. The airflow mechanics of the preconcentrator 19 are such that a low pressure exists in the plenum 45 and on the rear side of the porous impactor 42. As a result, the vaporized particles are transported from the porous impactor 42 into the low pressure plenum 45. A detector sample flow exhaust 52 is employed to generate a flow of the vaporized particles into the detector inlet 22. The volume of the plenum 45 partly determines the flow rate across the porous impactor 42, and hence also affects the concentration of particles. Thus, the volume of the plenum and the flow rate of the detector sample flow exhaust 52 preferably are small and are selected to achieve an optimum flow rate into the detector inlet 22. An alternative to the above-described porous impactor 42 can be formed with a sintered ceramic material that has the front surface plated with metal. An electric current then can be applied across the metallic material to heat the porous impactor 42 sufficiently to vaporize the particles impinging thereon.

The preconcentrator 19 illustrated in FIG. 3 utilized a continuous porous impactor 42 and diverts air around the periphery of the chamber 44 that contains the porous impactor 42. The porous impactors 42 of FIG. 3 is most effective for capturing particles that are entrained near the centerline of the flows stream A1. However, the momentum transfer is less for particles that are entrained in parts of the flow stream A1 further from the centerline. Thus, particles trajectories at more outward positions in the flow stream are less likely to divert from the flow stream. In this regard, the efficiency of particle impact will drop explanationally at further distances from the centerline of the flow stream A1. FIGS. 4 and 5 show an alternate preconcentrator 19A that effectively divides the preconcentrator 19A into several smaller areas. The alternate preconcentrator 19A includes a channel 36 similar or identical to the channel 36 illustrated in FIG. 3 and described above. However, several porous impactors 62 are mounted across the front of a chamber 64 to create a system of porous impactors 62 with multiple centerline flow patterns so that particles can impact more uniformally over the entire area of the preconcentrator 19A. The preconcentrator 19A illustrated in FIG. 5 may have an overall width of approximately 10 cm. However, each of the porous impactors 62 may have a width of about 1 cm and are separated from one another by channels 66 that communicate with the periphery of the chamber 64 to accommodate the main sample flow exhaust. The preconcentrator 19A of FIGS. 4 and 5 provides a different geometry and hence a different flow path for both air and particles. The geometry illustrated in FIGS. 4 and 5 can achieve greater sampling efficiency.

In both embodiments, the control 18 controls the operation of the detector 20 and generates an alarm signal if a particle of interest is detected.

While the invention has been described with respect to certain preferred embodiments, various changes can be made without deporting from the scope of the invention as defined by the claims. For example, the preconcentrator is shown as being used with a walk through detector portal. However, the preconcentrator can be used with other detection devices that rely upon transporting particles of the interest on a flow of air. The porous impactor also can take other geometries depending upon the sizes of the particles that are to be collected, flow rates of air towards the impactor and the dwell time targets. Additionally, an ion trap mobility spectrometer is shown as the detector. However, other detectors, including detectors that rely upon Raman spectroscopy can be employed.

What is claimed is:

1. An apparatus for detecting trace amounts of substances of interest comprising:

an inlet disposed for accommodating an air flow containing particles to be tested from a person or object to be sampled;

at least one outlet offset from said inlet for accommodating and diverting at least low inertial components of the air flow through the inlet;

at least one porous impactor at least partly aligned with the inlet for impaction by particles in the air flow having sufficiently high inertial characteristics; and a detector disposed for communicating with the impactor for identifying particles of interest on the impactor.

2. The apparatus of claim 1, wherein the impactor is substantially fixedly disposed with respect to the detector.

3. The apparatus of claim 2, further comprising a heater for heating the impactor sufficiently to vaporize particles impinging thereon.

4. The apparatus of claim 3, wherein the impactor comprises a metallic material and wherein the heater comprises an electric heater operative for directing a current through the metallic material of the impactor sufficient for heating the impactor.

5. The apparatus of claim 4, wherein the impactor comprises a sintered metallic material.

6. The apparatus of claim 4, wherein the impactor comprises a sintered non-metallic material and a metallic platting on at least one surface of the sintered non-metallic material.

7. The apparatus of claim 1, further comprising an air pump in communication with the outlet for generating a flow of air through the outlet substantially matched with a rate of air flow towards the inlet.

8. The apparatus of claim 1, further comprising a walk-through portal having side walls and a ceiling disposed relative to one another for accommodating a human pedestrian, the inlet being disposed in the ceiling for accommodating an air flow generated by a human convection plume of the human pedestrian in the portal, the impactor being gravitationally above the inlet.

9. The apparatus of claim 1, wherein the at least one impactor comprises a plurality of impactors spaced from one another, channels being defined between the impactors and providing communication between the inlet and the outlet.

10. The apparatus of claim 1, wherein the detector is an ion mobility spectrometer.

11. The apparatus of claim 1, wherein the detector is an ion trap mobility spectrometer.

12. The apparatus of claim 1, wherein the impactor is formed from a porous material, a chamber being mounted to the impactor for defining a plenum on a side of the impactor opposite the inlet, the detector communicating with the plenum.

13. An apparatus for detecting trace amounts of at least one substance of interest comprising:

a walk-through portal for accommodating a human pedestrian;

an inlet disposed gravitationally above the portal for receiving at least portions of an air flow generated by a human convection plume substantially surrounding the human pedestrian;

an outlet communicating with the inlet and offset from said inlet;

an air pump communicating with the outlet for generating a sample exhaust flow rate substantially matching a flow rate of air in the human convection plume;

at least one porous impactor substantially aligned with the inlet, said porous impactor being dimensioned and disposed for being impacted by particles entrained in portions of the human convection plume flowing through the inlet;

a heater for heating the porous impactor sufficiently for vaporizing particles impinging thereon;

a plenum communicating with a side of the porous impactor opposite the inlet; and a detector communicating with the plenum for receiving and analyzing vaporized particles that have impinged on the porous impactor.

14. The apparatus of claim 13, wherein the detector is an ion mobility spectrometer.

15. The apparatus of claim 13, wherein the detector is an ion trap mobility spectrometer.

16. The detector of claim 13, wherein the inlet, the porous impactor and the detector all are fixed relative to one another.

17. A method for detecting at least one substance of interest on a person or object, said method comprising:

passing an air flow in proximity to the person or object that is to be tested for the presence of the at least one substance of interest;

directing the air flow substantially along a first axis;

exhausting the air flow along a second axis offset from the first axis;

providing a porous impactor substantially along the first axis for impaction by particles entrained in the air flow;

continuously heating the porous impactor sufficiently to vaporize particles impacted thereon;

transporting the vaporized particles from the porous impactor to a detector; and substantially continuously operating the detector for identifying any substances of interest among the vaporized particles.

18. The method of claim 17, wherein the step of heating the porous impactor comprises heating the porous impactor to temperature of between approximately 220° C.–250° C.

19. The method of claim 17, wherein the step of exhausting the air flow through the outlet comprises exhausting the air flow at at least about 50 liters/second.

20. The apparatus of claim 12, further comprising an exhaust air pump in communication with the outlet for generating a flow of air through the outlet substantially matched with a rate of air flow towards the inlet, the apparatus further comprising a detector air pump that communicates with an outlet from the plenum, the detector air pump producing a lower flow rate than the exhaust air pump.

* * * * *